United States Patent
Duquet et al.

(10) Patent No.: US 7,216,781 B2
(45) Date of Patent: May 15, 2007

(54) FLUID DISPENSER

(75) Inventors: Frédéric Duquet, Thibouville (FR); Firmin Garcia, Evreux (FR); Alex Milian, Breteuil sur Iton (FR)

(73) Assignee: Valois SAS, Le Neubourg (FR)

( * ) Notice: Subject to any disclaimer, the term of this patent is extended or adjusted under 35 U.S.C. 154(b) by 272 days.

(21) Appl. No.: 10/645,664

(22) Filed: Aug. 22, 2003

(65) Prior Publication Data
US 2004/0065688 A1    Apr. 8, 2004

Related U.S. Application Data

(60) Provisional application No. 60/427,576, filed on Nov. 20, 2002.

(30) Foreign Application Priority Data
Aug. 23, 2002    (FR) .................................. 02 10550

(51) Int. Cl.
*B65D 37/00*    (2006.01)
(52) U.S. Cl. ...................................... 222/206; 222/215
(58) Field of Classification Search ................ 222/206, 222/215, 209, 214, 103, 633; 383/906
See application file for complete search history.

(56) References Cited

U.S. PATENT DOCUMENTS

| | | | | |
|---|---|---|---|---|
| 1,360,642 | A * | 11/1920 | Irwin | 222/633 |
| 1,438,487 | A * | 12/1922 | Greene | 222/215 |
| 2,096,920 | A * | 10/1937 | Rose | 222/214 |
| 2,432,288 | A * | 12/1947 | Danziger | 222/83 |
| 2,915,222 | A * | 12/1959 | Purinton | 222/175 |
| 3,179,301 | A * | 4/1965 | Lucht | 222/213 |
| 3,412,907 | A * | 11/1968 | Faso | 222/187 |
| 4,898,306 | A * | 2/1990 | Pardes | 222/206 |
| 4,990,016 | A | 2/1991 | Seidler | |
| 5,226,564 | A * | 7/1993 | Steer et al. | 222/107 |
| 5,356,039 | A * | 10/1994 | Christine et al. | 222/107 |
| 5,950,871 | A | 9/1999 | De Pous et al. | |

FOREIGN PATENT DOCUMENTS

| FR | 2 781 770 A1 | 2/2000 |
|---|---|---|
| FR | 2 791 645 A1 | 10/2000 |
| GB | 626 631 A | 7/1949 |

* cited by examiner

*Primary Examiner*—Philippe Derakshani
(74) *Attorney, Agent, or Firm*—Sughrue Mion, PLLC

(57) ABSTRACT

A fluid dispenser (100; 200; 300; 400) for dispensing a fluid in liquid or in powder form, the dispenser including a reservoir (12) serving to contain fluid, and a dispensing orifice (114; 214; 314; 414) via which the fluid is dispensed. The reservoir (12) having an actuating wall (111; 211; 311; 411) and a backing wall (112; 212; 312; 412), the walls be adapted to be brought towards each other by elastic deformation to reduce the volume of the reservoir, and thus to deliver fluid through the dispensing orifice. The dispenser further having a one-piece body (110; 210; 310; 410) and at least one flexible sealing film (120; 220; 320; 421; 422), the actuating wall and the backing wall being formed by the one-piece body, wherein the actuating wall and the backing wall are angularly positioned relative to each by forming an angle that decreases when they are brought towards each other.

26 Claims, 7 Drawing Sheets

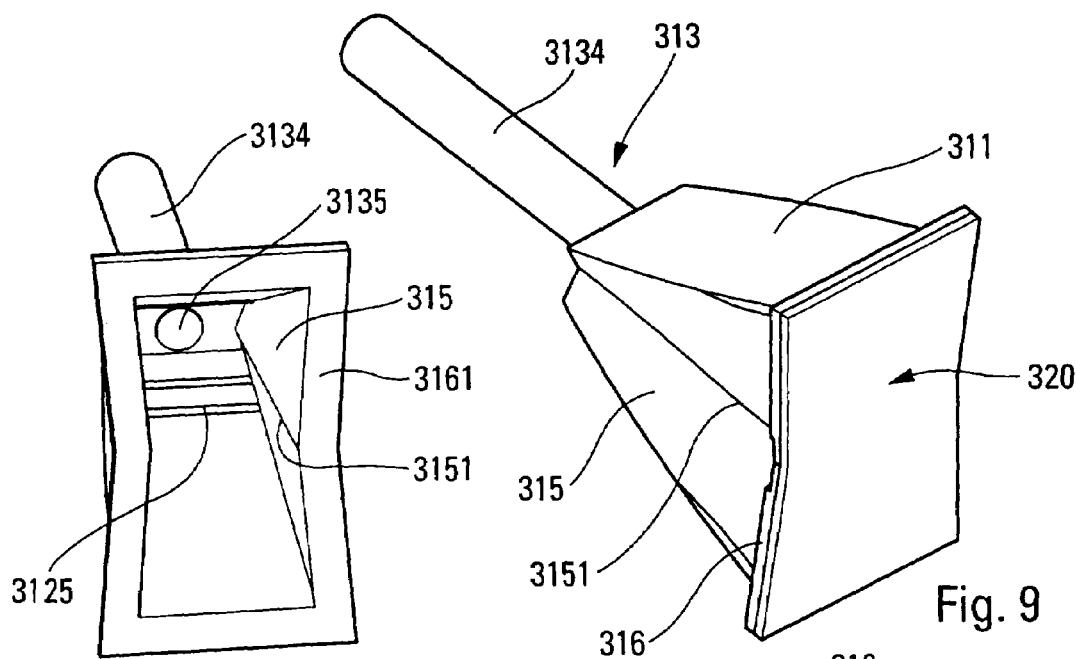
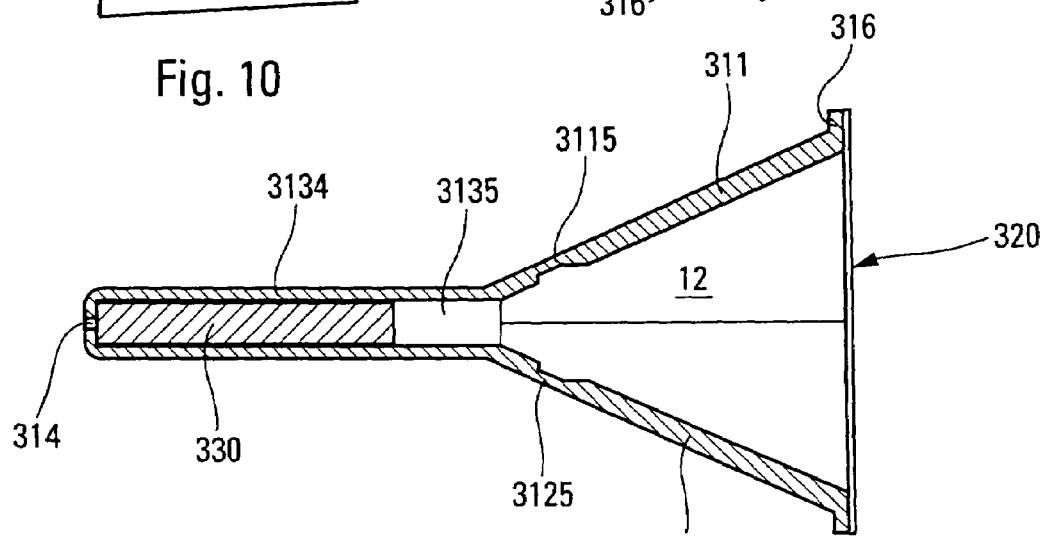
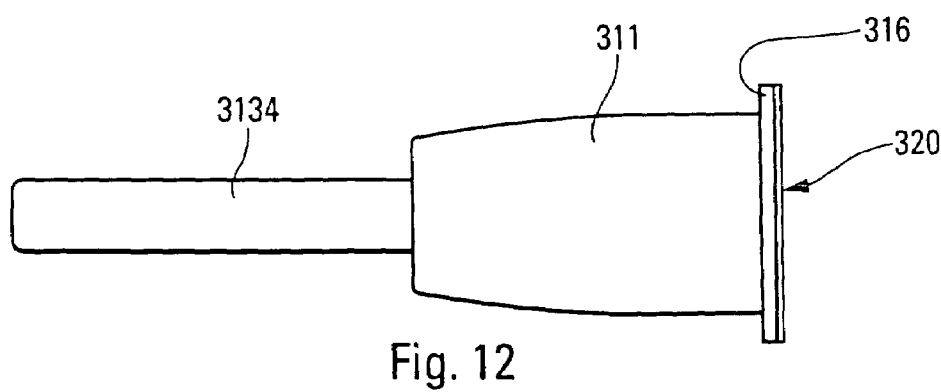

FLUID DISPENSER

CROSS REFERENCE TO RELATED APPLICATION

This application claims the benefit under 35 U.S.C. §119 (e) of pending U.S. provisional patent application Ser. No. 60/427,576, filed Nov. 20, 2002, and priority under 35 U.S.C. §119(a)–(d) of French patent application No. FR-02.10550, filed Aug. 23, 2002.

BACKGROUND OF THE INVENTION

The present invention relates to a fluid dispenser for dispensing a fluid in liquid or in powder form, i.e. a liquid of various degrees of viscosity, or a powder, contained in a reservoir. The dispenser is provided with a dispensing orifice via which the fluid is dispensed. To this end, the reservoir has an actuating wall and a backing wall, said walls being adapted to be brought towards each other by elastic deformation to reduce the volume of the reservoir, and thus to deliver fluid through the dispensing orifice. This type of dispenser is in frequent use in numerous fields, and in particular in cosmetics, perfumes, or indeed pharmaceuticals.

Fluid dispensers of this type are used, inter alia, in the fields of pharmaceuticals and of cosmetics as product samples which can, for example, be distributed free of charge to enable consumers to test the product before they purchase it. Documents FR 2 778 639 and FR 2 791 645 describe such dispensers that are mainly but not exclusively used as samples. In the dispensers of those documents, provision is made to seal together two films or to seal a shell to a film around their peripheries to define a fluid reservoir. Those documents also make provision to insert a dispensing part between the two films or between the shell and the film. The dispensing part defines the dispensing orifice and optionally serves as support means for supporting a piece of porous material suitable for being soaked with fluid. To actuate those dispensers, the films or the shell define a deformable actuating wall suitable for being pressed by one or more fingers. When the dispenser comprises two sealed-together films, there are two actuating walls, and it is possible, for example, to actuate the dispenser by holding it between the thumb and one or more fingers of the same hand. The wall in contact with the thumb thus defines the actuating wall, while the wall in contact with the other finger(s) of the same hand serves as a backing wall making it possible to exert thrust on the wall in contact with the thumb. Similarly, when the dispenser comprises a shell fixed to a film, the thumb comes into contact with the shell which defines the actuating wall while the other fingers of the same hand come into contact with the sealing film which thus serves as a backing wall to enable thrust to be exerted on the actuating wall by using the thumb. Thus, in both of those prior art dispensers, the actuating wall and the backing wall are formed by two separate parts, while the dispensing orifice is formed by a third part.

In a technical field that is somewhat remote, Document GB 626 631 describes a carton of insecticide making it possible to spray powder that it contains. For that purpose, the carton is in the form of a bellows defining two actuating walls that can be brought towards each other by pivoting about a coupling portion that defines the spray orifice. However, to impart an elasticity or return characteristic to that carton, a metal spring is disposed inside the carton so as to urge the two actuating walls apart. Thus, in the rest position, the two actuating walls are spaced apart to the maximum extent, and they can be brought towards each other by compressing the spring situated inside the carton. In that document, the two actuating walls are formed by two pieces of cardboard connected at one end to a block of wood defining a hole in which a metal nozzle is inserted. The V-shaped spring is inserted between the two pieces of cardboard and the resulting assembly is wrapped in one or more layers of flexible material, e.g. foil. Thus, the flexible foil covers the two pieces of cardboard and thereby defines the two actuating walls. In all, the prior art dispenser described in that document is made up of six distinct component elements.

SUMMARY OF THE INVENTION

An object of the present invention is to remedy the drawbacks suffered by the above-mentioned prior art by defining a novel fluid dispenser for dispensing fluid in liquid or powder form, which dispenser also operates on the mechanical bellows principle but incorporates as small a number of component parts as possible so that it is very simple to assemble.

To this end, the present invention provides a fluid dispenser for dispensing a fluid in liquid or in powder form, said dispenser including a reservoir serving to contain fluid, and a dispensing orifice via which the fluid is dispensed, said reservoir having an actuating wall and a backing wall, said walls be adapted to be brought towards each other by elastic deformation to reduce the volume of the reservoir, and thus to deliver fluid through the dispensing orifice, said dispenser further comprising a one-piece body and of at least one flexible sealing film, the actuating wall and the backing wall being formed by the one-piece body, characterized in that the actuating wall and the backing wall are angularly positioned relative to each by forming an angle that decreases when they are brought towards each other. Advantageously, the dispensing orifice is formed by the one-piece body. Thus, the one-piece body on its own forms the actuating wall and the backing wall, and the dispensing orifice. Preferably, the elastic deformation is provided by the one-piece body which has elastic resilience suitable for returning it to a rest position, in which the actuating wall is as far away as it can be from the backing wall. Thus the one-piece body performs almost all of the dispenser functions on its own, except for the function inherent to the flexible sealing film that makes it possible to complete the reservoir while also deforming when the actuating and backing walls are brought towards each other.

According to an advantageous characteristic of the invention, the body defines a head portion which remains substantially static while the actuating wall and the backing wall are being brought elastically towards each other, the dispensing orifice being formed by the head portion. In which case, the actuating wall may be hinged elastically to the head portion. Advantageously, the actuating wall is mounted to pivot relative to the backing wall. In a variant, the actuating wall is elastically deformable. Preferably, the backing wall is symmetrically identical to the actuating wall about the head portion.

According to another characteristic, the actuating wall and the backing wall converge mutually at the head portion.

In another aspect, the actuating wall and the backing wall are substantially plane and rigid.

According to another advantageous characteristic of the invention, the dispenser includes a piece of porous material suitable for being impregnated with fluid, said piece being disposed adjacent to the dispensing orifice. Advantageously, the body defines a head portion forming the dispensing orifice, said portion forming retaining means for holding the piece of porous material adjacent to the dispensing orifice. The piece of porous material is particularly useful when the fluid is in liquid form, but it is also possible to imagine embodiments in which a piece of porous material is also used that is suitable for being impregnated with a powder before said powder is dispensed through the dispensing orifice.

In another aspect, the head portion forms an elongate end-piece at the free end of which the dispensing orifice is formed. The elongate end-piece is particularly useful when the dispenser serves as a spray, e.g. a nasal spray, in which the end-piece serves as an applicator to be inserted into an orifice of the body, e.g. a nostril.

In a practical embodiment, the actuating wall and the backing wall are interconnected by deformable side panels.

In another aspect, the body is provided with at least one plane peripheral fixing zone to which a plane sealing film is fixed. This applies particularly when the actuating and backing walls are provided with deformable coupling side panels. In which case, a single plane sealing film suffices.

For example, the body may be made by injection molding, but it may also be made from a plane sheet that is cut and then folded, the dispensing orifice being situated at the fold. In a variant, the body may also be made from an extruded shaped-section member.

In another embodiment, the actuating wall and the backing wall are connected together via an elastically deformable coupling web formed by the one-piece body. This coupling serves to impart, by itself, or to improve the elastic deformation characteristic of the body making it possible to return the actuating and backing walls to their rest position.

Such a dispenser may be made up only of the one-piece body, of one or more sealing films, and optionally of a piece of porous material suitable for being impregnated with fluid. It is thus possible to imagine a dispenser made up only of a one-piece body and of a single sealing film, it being possible to omit the piece of porous material in certain applications.

BRIEF DESCRIPTION OF THE DRAWINGS

The invention is described more fully below with reference to the accompanying drawings which show four embodiments of the invention by way of non-limiting example.

In the figures:

FIG. 9 is a perspective view of a third embodiment of a dispenser of the invention;

FIG. 10 is a view inside the dispenser of FIG. 9 when the sealing film is removed;

FIG. 11 is a view in vertical section through the dispenser of FIG. 9;

FIG. 12 is a plan view of the dispenser of FIG. 9;

DETAILED DESCRIPTION OF A PREFERRED EMBODIMENT

Figure 1:
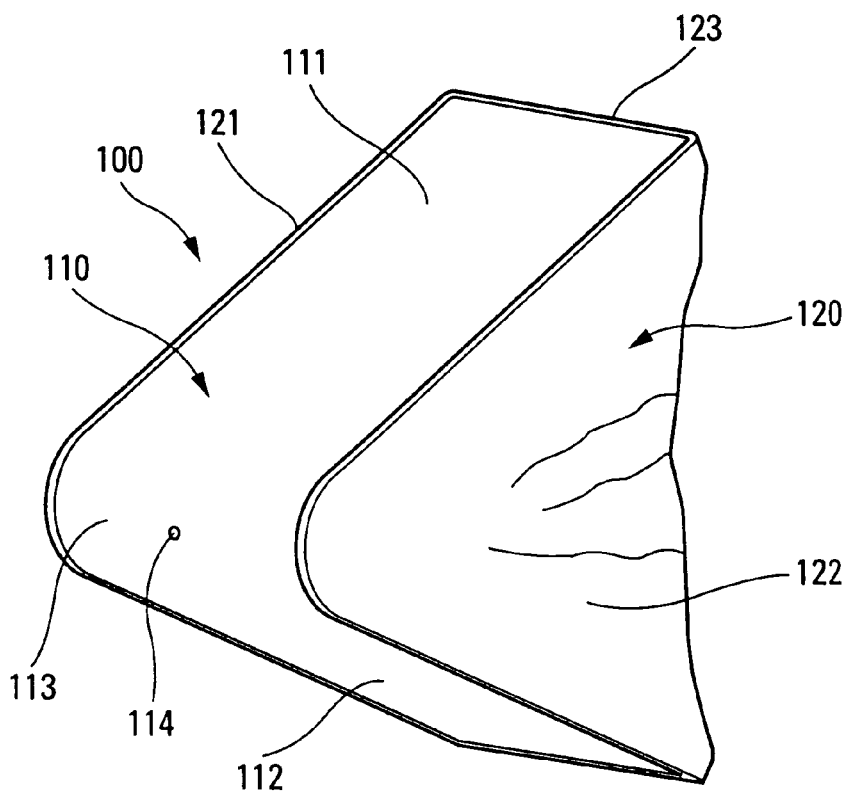
FIG. 1 is a perspective view of a first embodiment of a dispenser of the invention.

In all four of the embodiments described below, the dispensers are more particularly suitable for dispensing a fluid in liquid form, but they may also dispense a fluid in powder form. All four embodiments are in the overall form of a bellows having an actuating wall on which it is possible to press, e.g. with the thumb, and a backing wall which can be in contact with one or more fingers of the same hand, so that it is possible to bring the actuating wall closer to the backing wall by pressing on the actuating wall with the thumb. However, a dispenser of the invention may also be actuated by means other than a hand, e.g. by a mechanical device. Similarly, in all four embodiments, the dispenser defines a reservoir containing both a liquid or a powder, and also a gas, which, in general, is air. Naturally other gases, e.g. inert gases, may be used for certain applications, e.g. for pharmaceuticals. Because the reservoir contains both a liquid or a powder and a gas, the dispensing performed by a dispenser of the invention is in the form of a two-phase sprayed jet in which fine droplets of fluid are conveyed by a flow of air ejected under pressure. However, the reservoir may contain liquid or powder only, so that the dispensing is in the form of a continuous stream or of a sprayed jet, or else in the form of a drop that is collected, e.g. by using a finger.

With reference more particularly to FIGS. 1 to 4, which show the first embodiment of the invention, it can be seen that the dispenser 100 is made up of three component parts, namely a one-piece body 110, a sealing film 120, and a piece of porous material 130. In certain applications, it is possible to omit the piece of porous material 130, so that the dispenser is then made up of only two component parts, namely the one-piece body 110, and the sealing film 120.

The one-piece body 110 is in the general shape of a clip made up of two blades, namely a first blade 111 connected to a second blade 112 via a coupling portion 113. The blades 111, 112 may be of any shape, i.e. polygonal or rounded. The coupling portion 113 is preferably folded over in rounded manner without forming a sharp fold. However, it is possible to imagine a coupling portion 113 that has a substantially plane wall defined by two side edges from which the two blades 111 and 112 extend. In the embodiment used to illustrate the present invention, each of the blades 111 and 112 is substantially elongate rectangle shaped so that each blade is connected to the coupling portion 113 via a short side of the corresponding rectangle. The other short side of the rectangle defines a free end of the blade. Each blade thus has three edges. More precisely, the blade 111 has two side edges 1111 and 1112 and an end edge 1113. Symmetrically, the blade 112 has two side edges 1121 and 1122 and an end edge 1123. These edges are preferably of some width, which defines the thickness of the blades, in this example. However, it is possible to imagine embodiments in which each blade is provided with flaps defining the edges of the blades. In the example shown in FIGS. 1 to 4, he height of the edges corresponds to the thickness of the blades. In addition, said thickness is constant over both blades and also over the coupling portion 113. In other words, the one-piece body has a wall thickness that is constant. However, variant embodiments may be imagined in which the thickness of the blades and of the coupling portion varies: e.g., the coupling portion 113 may be of thickness greater than the thickness of the blades at the end edges 1113 and 1123. Furthermore, in the embodiment shown in FIGS. 1 to 4, the one-piece body 110 is fully symmetrical about the coupling portion 113 so that the blades 111 and 112 are symmetrically identical. It is quite possible to make provision for the two blades 111 and 112 not to be identical. For example, it is possible to make provision for the blade 112 to have a wall thickness or a shape different from the wall thickness or from the shape of the blade 111. It is also possible to imagine the blade 112 being connected to the coupling portion 113 in a manner differently from the manner which the blade 111 is connected thereto.

Figure 2:
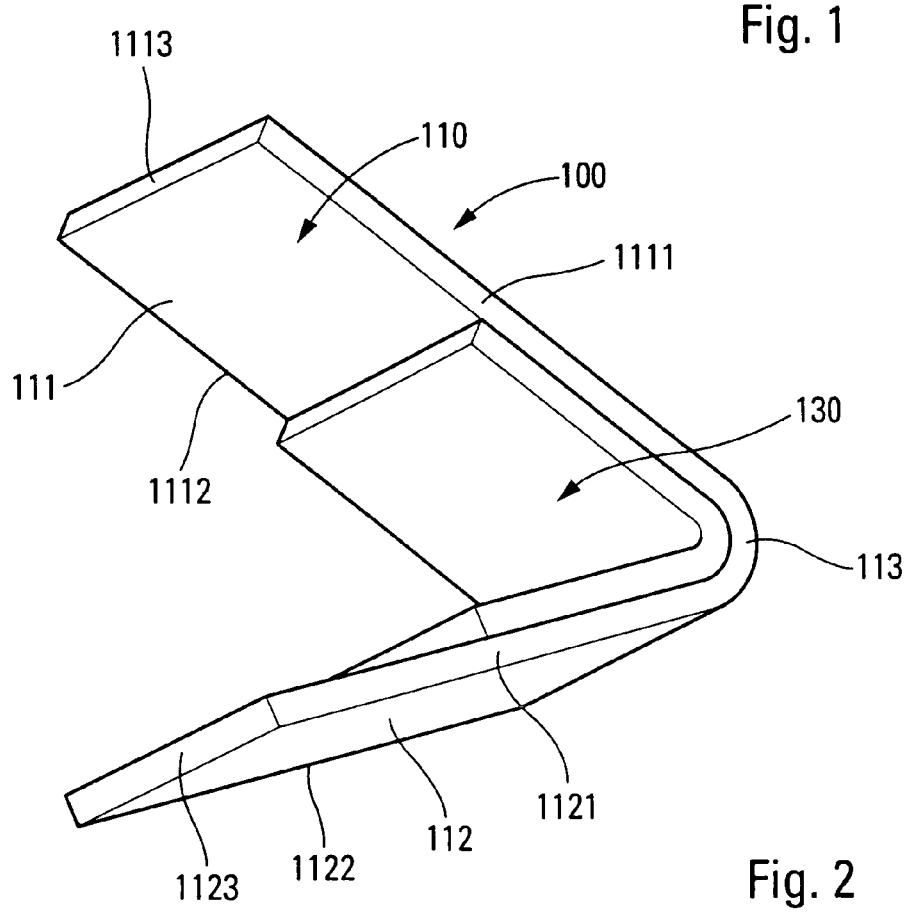
FIG. 2 is a perspective view of the dispenser of FIG. 1, with the sealing film removed.
Figure 3:
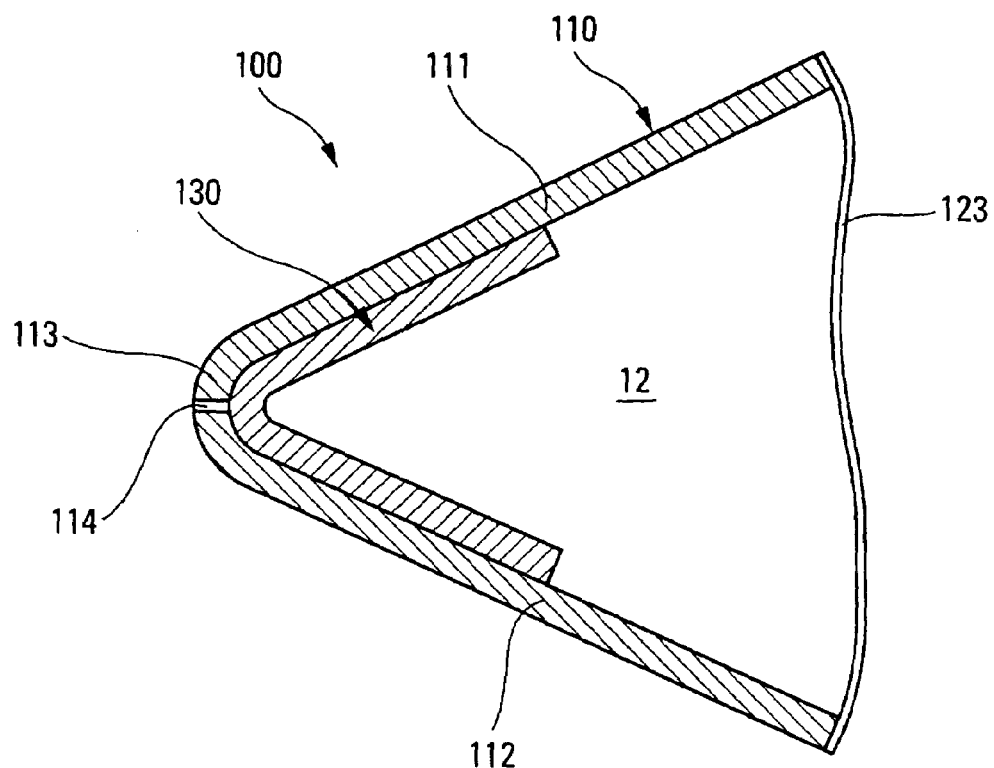
FIG. 3 is a view in vertical section through the dispenser of FIG. 1.
Figure 4:
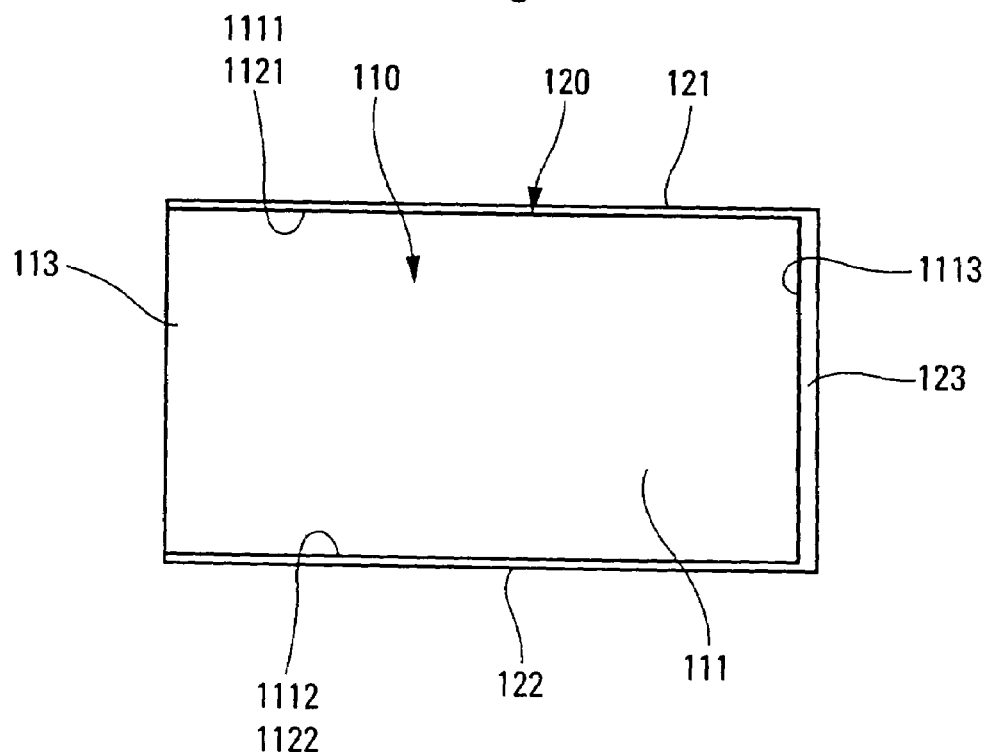
FIG. 4 is a plan view of the dispenser of FIG. 1.
Figure 5:
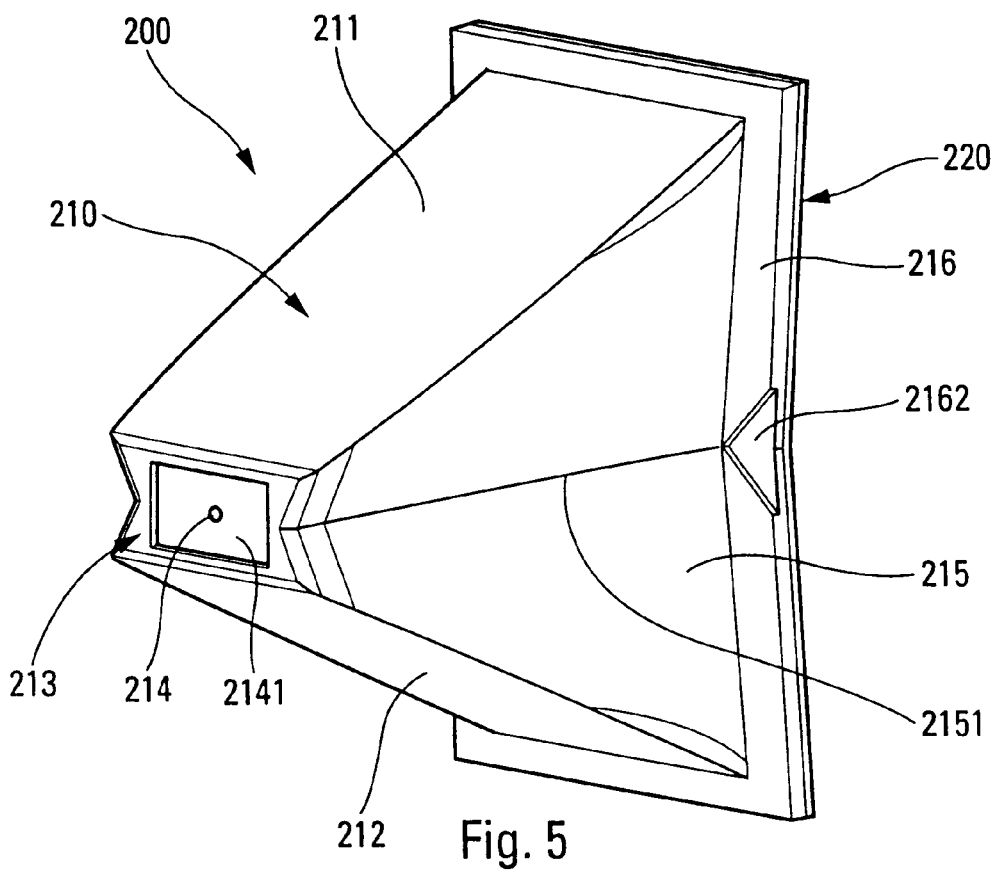
FIG. 5 is a perspective view of a second embodiment of a dispenser of the invention.

The one-piece body 110 has an elastic deformation characteristic such that the blade 111 can be brought towards the blade 112 from a rest position, which is the position shown in FIGS. 1 to 3. In the rest position, the blade 111 forms a maximum angle relative to the blade 112. In other terms, the blade 111 converges towards the blade 112 at the coupling portion 113 that interconnects them. The elastic resilience of the one-piece body 110 is imparted in part or in full by the coupling portion 113, whose rounded shape can be accentuated by elastic deformation. The blades 111 and 112 are preferably plane and rigid so that they can pivot about the coupling portion 113 substantially without being deformed. It is also possible to imagine embodiments in which the blades 111 and 112 also have an elastic deformation characteristic which participates in or imparts the elastic deformation characteristic of the one-piece body 110. In the latter case, provision may be made for the coupling portion 113 to be substantially rigid and non-deformable. It can thus be understood that the one-piece body 110 has a certain amount of elastic resilience that is intrinsic or inherent to it, without it being important to determine which portion of the one-piece body imparts the elastic deformation characteristic. It is possible to imagine the one-piece body forming one or more flexible tabs that extend between the two blades 111 and 112, and that impart or improve the elastic deformability of the one-piece body. Thus, regardless of the manner in which the elastic deformation characteristic is achieved, it is important for it to be possible for the two blades 111 and 112 to be brought towards each other from the rest position by overcoming the elastic resistance inherent to the one-piece body. In practice, the one-piece body 110 may be grasped in a hand so that the blade 111 comes into contact with the thumb, and so that the blade 112 comes into contact with one or more fingers of the same hand, the finger(s) thus acting against the thumb. It is thus possible to exert pressure on the blade 111 by using the thumb, so that the blade 111 acts as the actuating wall, while the wall 112 that remains in abutment against one or more fingers of the same hand acts as a backing wall enabling the thumb to exert pressure on the actuating wall. Thus, in the invention, the blade 111, or more precisely its outside wall, forms an actuating wall while the outside wall of the blade 112 forms a backing wall. The coupling portion 113 forms a head portion defining a dispensing orifice 114. It can also be noted that, while the two walls are being brought together, the head portion 113 remains substantially static so that the dispensing orifice also remains static. Naturally, as soon as the pressure on the actuating wall 111 is released, the one-piece body 110 returns to its rest position because of the elastic deformation characteristic that imparts a shape memory to the one-piece body.

The one-piece body 110 is preferably made of a plastics material, but it may also be made of other materials, such as metal, for example. It is also possible to imagine the one-piece body being made of a plurality of materials, such as, for example, a metal blade coated with some other material such as plastic. As mentioned above, the one-piece body shown in FIGS. 1 to 3 is of constant wall thickness, so that it is very simple to make by cutting out a strip from a sheet. The strip is then folded over to form the two blades 111 and 112 and the coupling portion 113 that forms the fold. It is then necessary merely to provide an orifice in the coupling portion. It is also possible to imagine the one-piece body being made from a sort of extruded, shaped-section, or even molded angle bar, with the angle bar defining two longitudinal flanges that extend relative to each other at an acute angle and that are connected together via a coupling portion. It is then necessary merely to cut slices from the angle bar to obtain a one-piece body as shown in FIGS. 1 to 3. The solution using an angle bar makes it possible to cause the wall thickness of the one-piece body to vary at the various places. It also is possible to imagine the one-piece body being made by a conventional injection molding method.

Optionally, in the invention, the one-piece body 110 may be provided with a piece of porous material 130 that is disposed adjacent to the dispensing orifice 114, as can be seen very clearly in FIG. 3. The piece of porous material 130 has absorbance characteristics enabling the porous material to be impregnated with fluid, be it in liquid or in powder form. However, the use of such a piece of porous material is more particularly adapted to dispensing liquid. In the example shown in FIGS. 2 and 3, the piece of porous material is in the form of a strip or tongue that is fixed between the two blades 110 and 111 by any suitable known means, such as, for example, adhesive bonding, or sealing. The piece of porous material 130 therefore extends over portions of the inside faces of the blades 111 and 112, and over the inside face of the coupling portion 113 in which the dispensing orifice 114 is formed. The piece of porous material 130 may be mounted on the one-piece body 110 before it is folded over, when the body is made from a sheet, or even during manufacture of the above-mentioned angle bar. It should be well understood that the piece of porous material 130 is not an essential component element of the present invention, and that it is therefore possible to omit it in certain applications, particularly for dispensing powder.

In the invention, the one-piece body 110, optionally provided with a piece of porous material 130, is provided with a sealing film 120 which is fixed in leaktight manner, e.g. by adhesive bonding or sealing, to the one-piece body 110 along the edges 1111, 1112, 1113, 1121, 1122, and 1123 of the blades 111 and 112. It is important for the sealing film 120 to be fixed in leaktight manner so as to define a leaktight internal volume which, in the invention, serves as fluid reservoir 12. The reservoir may be fully filled with fluid, or preferably it may be filled with a small quantity of fluid, the remainder of the volume of the reservoir being filled with gas, e.g. air. The sealing film 120 is flexible and is freely deformable without too much elasticity or shape memory, so that the blades 111 and 112 can be brought towards each other by deforming or by creasing the sealing film 120. A sort of conventional bellows is thus formed, making it possible to dispense fluid with or without an additional stream of gas. However, the bellows is not provided with an inlet valve, the air penetrating through the dispensing orifice into the reservoir 12 when the one-piece body 110 relaxes towards its rest position.

To fix the sealing film 120 properly to the edges of the one-piece body 110, it is advantageous for said edges to have some height or thickness because they define fixing or application zones for the sealing film. The preferred fixing technique is sealing. It should be noted that the fixing zones for fixing the sealing film extend substantially in three distinct planes, namely a first plane formed by the edges 1111 and 1121, a parallel second plane formed by the edges 1112 and 1122, and a perpendicular third plane formed by the edges 1113 and 1123, as can be seen more clearly in FIG. 4.

This first embodiment of the dispenser may be used advantageously as a fluid product sample, e.g. made available free of charge to consumers so that they can test the product before deciding whether to buy it.

Reference is made below to FIGS. 5 to 8 which show a second embodiment of the invention.

The second embodiment reproduces certain general characteristics of the first embodiment. In particular, the second embodiment of the dispenser 200 also has a one-piece body 210 optionally provided with a piece of porous material 230, and associated with a sealing film 220. The one-piece body 210, which, in this example, is preferably made of an injection-molded plastics material, is made up of two blades 211 and 212 interconnected via a head portion 213 in which the dispensing orifice 214 is provided. The head portion 213 also serves to couple together the two blades 211 and 212. Preferably, the blades are substantially plane and rigid, and, in this example, they are hinged at two bridges 2115 and 2125 to the head 213 which is substantially rigid in this example. The head forms a sort of recess 2141 in the end wall of which the dispensing orifice 214 is provided. The recess 2141 may serve to receive a removable closure member serving to close off the dispensing orifice 214 in leaktight manner before the dispenser is used for the first time, or between occasions on which it is used. Internally, the head 213 forms retaining means 2133 serving to hold the piece of porous material 230 in place on the head 213 and between the blades 211 and 212. The hinge bridges 2115 and 2125 may be elastically deformable, so that the blades 211 and 212 then tend to return to a rest position, which is the position shown in FIGS. 5 to 7. However, the hinge bridges may also be fully flexible, i.e. without any shape memory.

In the invention, the one-piece body 210 is further provided with side panels 215 that connect the blades 211 and 212 together. More precisely, one side panel 215 extends from the head 213 and joins together the right side edges of the blades 211 and 212. Symmetrically, another side panel 215 also extends from the head 213 and joins together the left side edges of the blades 211 and 212. In this way, the one-piece body 210 forms a sort of conical cornet having four faces formed by the two blades 211 and 212, and by the two side panels 215, the tip being formed by the head portion 213. In the invention, each side panel 215 is deformable and preferably elastically deformable, so that it does not prevent the blades 211 and 212 from moving towards each other by pivoting about the bridges of material 2115 and 2125. Indeed the side panels 215 preferably have an elastic deformation characteristic making it possible to impart a resilient return function to the one-piece body, as in the first embodiment. In a practical form of the second embodiment, each side panel 215 may be provided with a fold line 2151 which tends to move towards the inside of the one-piece body when the two blades 111 and 112 are moved towards each other. To guarantee that the fold lines 2151 move inwards, and as can be observed, the side panels 215 are not exactly plane, but rather they are slightly inwardly curved to predetermine the direction in which the fold lines 2151 move. Thus, when the blade 211 is moved towards the blade 212, the two fold lines 2151 tend to be moved towards the inside of the one-piece body 210. This can be understood easily by looking at FIG. 6. The elastic deformation or return characteristic of the one-piece body 210 may be achieved by the side panels 215 only, or by the bridges of material 2115 and 2125 only, or by a combination of both. In the second embodiment, the head portion 213 does not participate in or hardly participates in the elastic deformation or return characteristic of the one-piece body 210.

Figure 6:
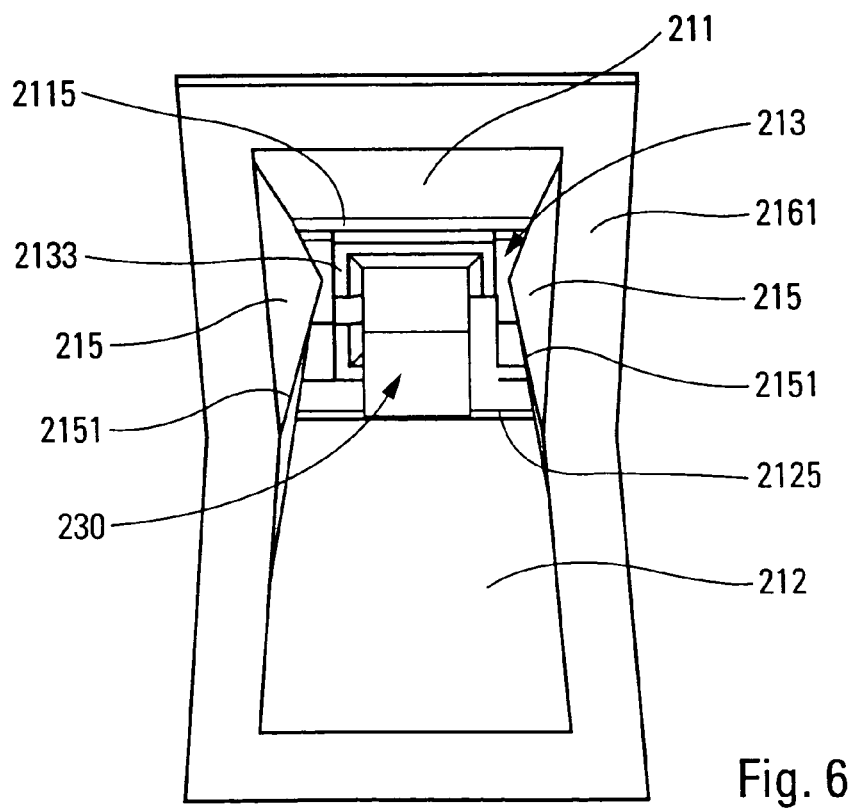
FIG. 6 is a view inside the dispenser of FIG. 5 when the sealing film is removed.
Figure 7:
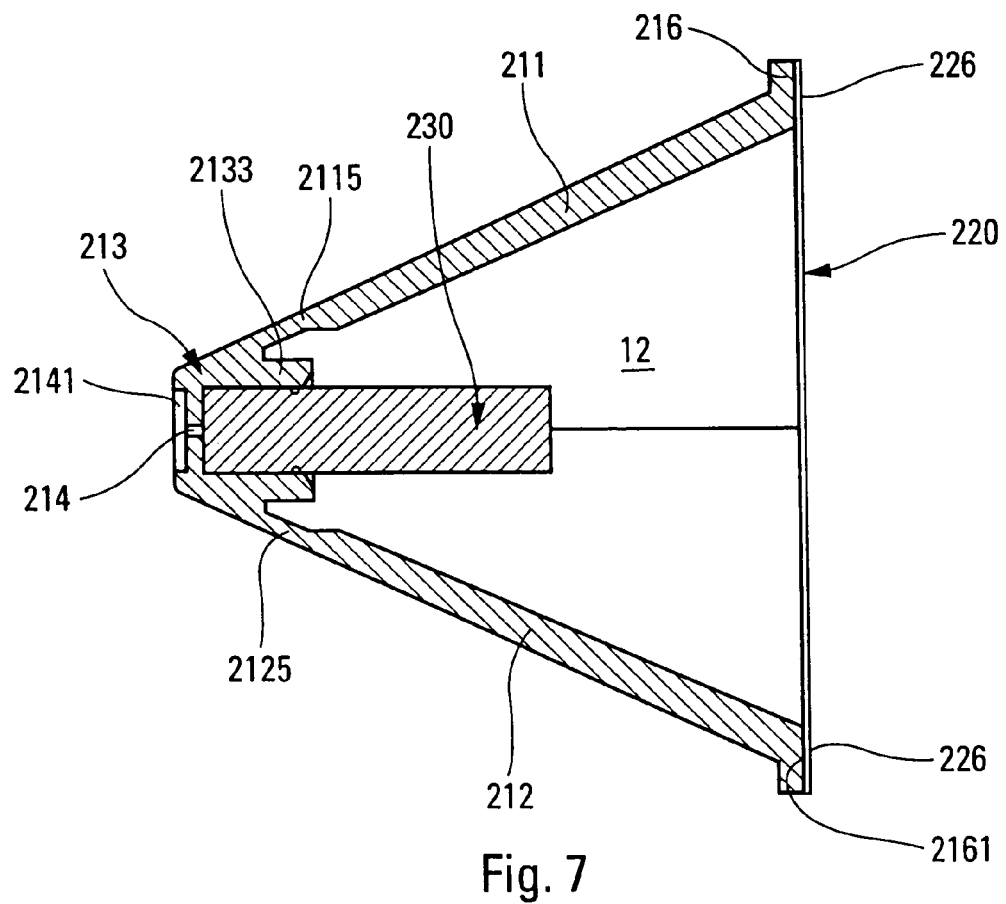
FIG. 7 is a view in vertical section through the dispenser of FIG. 5.
Figure 8:
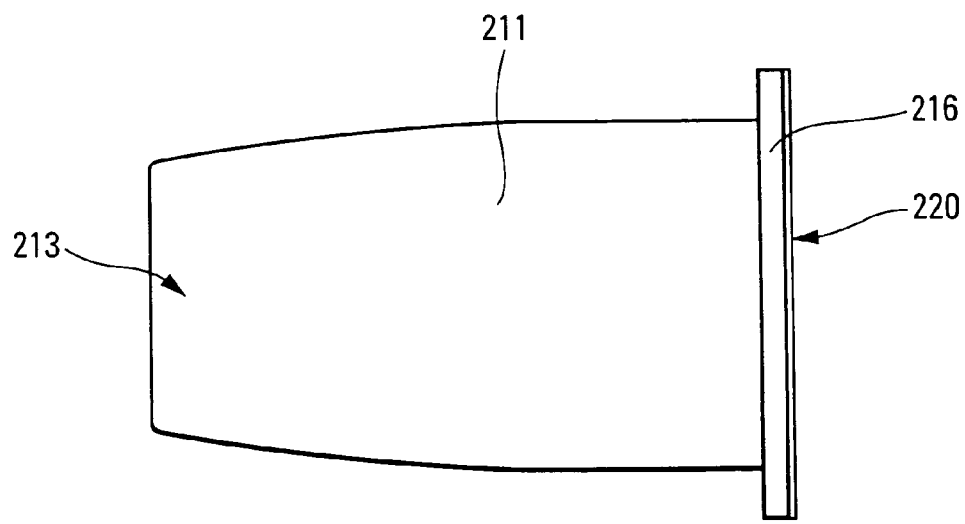
FIG. 8 is a plan view of the dispenser of FIG. 5.
Figure 13:
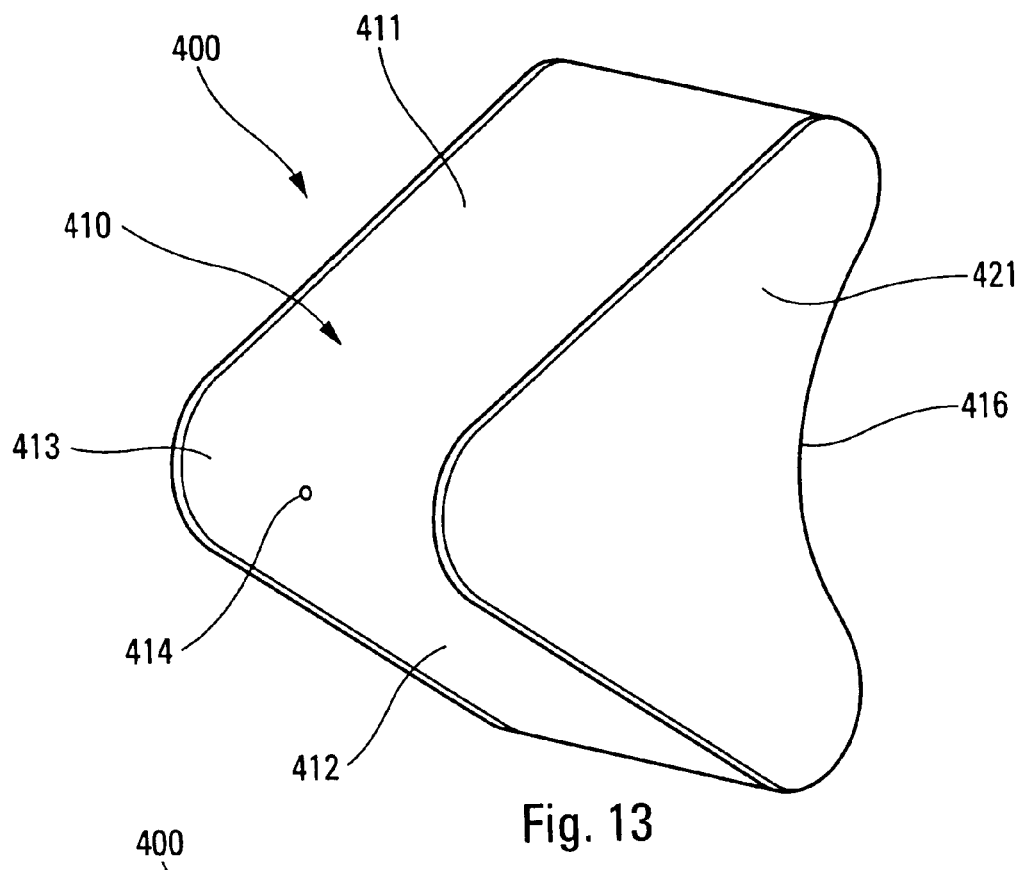
FIG. 13 is a perspective view of a fourth embodiment of a dispenser of the invention.
Figure 14:
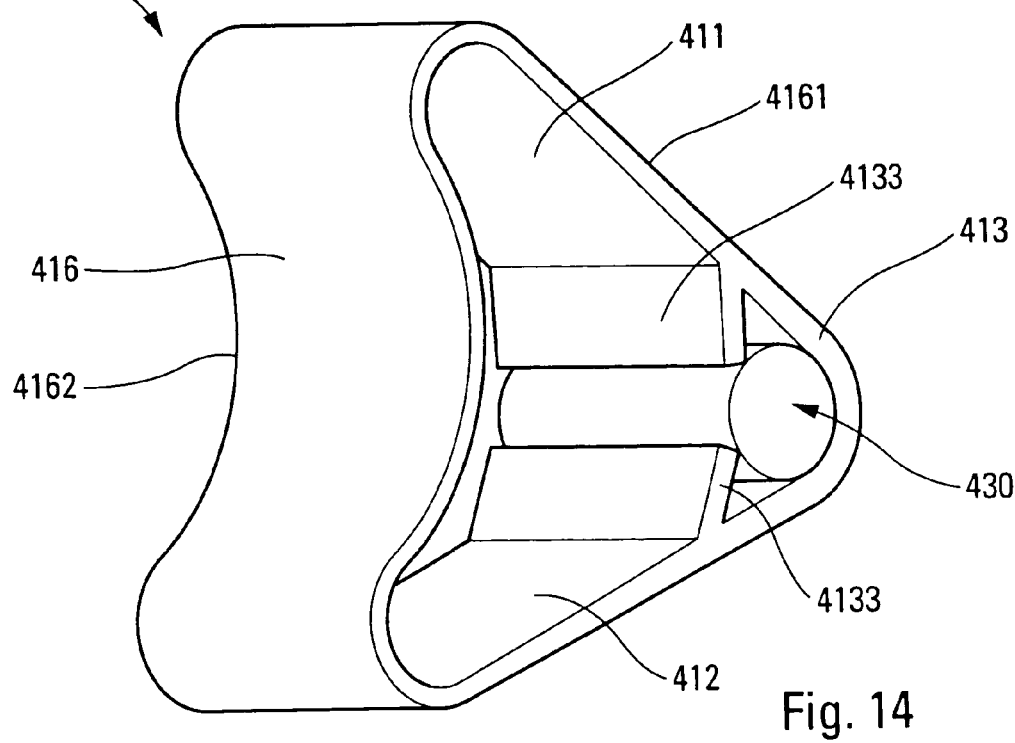
FIG. 14 is a view of the dispenser of FIG. 13 when at least one sealing film is removed.
Figure 15:
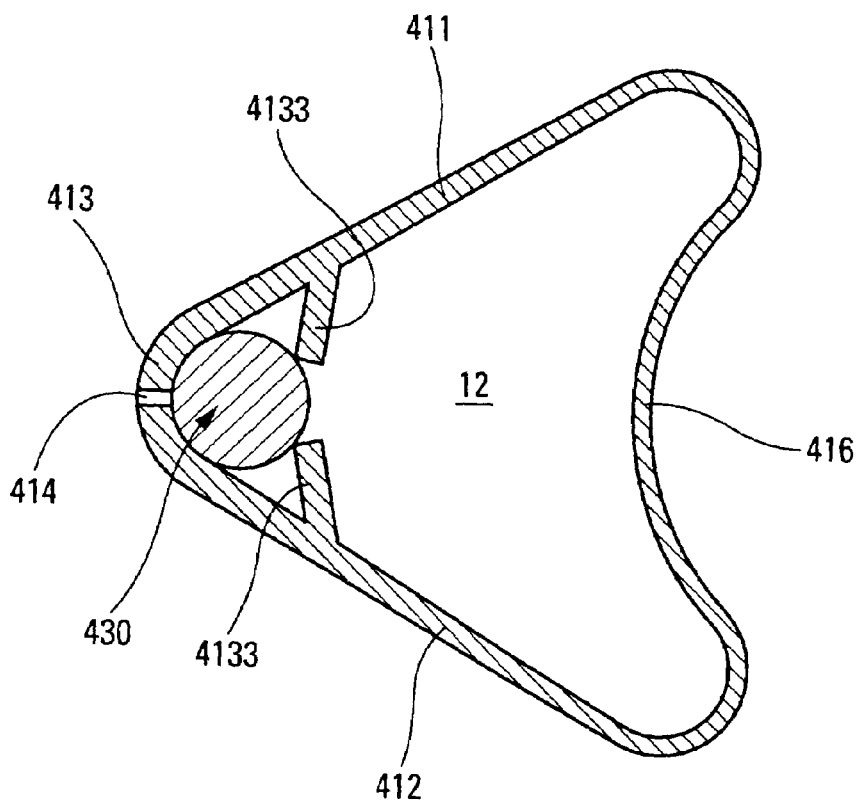
FIG. 15 is a view in vertical section through the dispenser of FIG. 13.

At their ends opposite from the head portion 213, the blades 211 and 212, and the side panels 215 form a rim 216 which, in this example, is in the form of a frame that is substantially rectangular, as can be seen in FIG. 6. However, the long sides of the rectangle are deflected slightly inwards because of the angular positions of the fold lines 2151. However, the rim 216 forms a fixing or application surface or zone 2161 that is fully plane, as can be seen in FIGS. 7 and 8. The fixing or application surface 2161 serves for fixing a sealing film 220 which may advantageously be fixed to the one-piece body 210 under fully plane conditions. The sealing film 220 is fixed to the surface 261 at its outer periphery 226, as can be seen in FIG. 7. It is particularly advantageous for the fixing surface or zone 2161 of the one-piece body 210 to be fully plane for technical fixing or sealing reasons because the applicator element can then be fully plane.

Once the sealing film 220 is fixed, an internal volume is thus defined that serves as a reservoir 12, which may contain liquid or powder only, or also a gas, such as air. As in the first embodiment, the piece of porous material 230 is in direct contact with the fluid inside the reservoir 12. However, in certain cases, it is possible to omit the piece of porous material 230. Thus, by pressing on the blade 211 which serves as an actuating wall, and by holding the blade 212 substantially stationary so that it serves as a backing wall, it is possible to move the blade 211 towards the blade 212 by means of the bridges 215 and 225 deforming flexibly, thereby reducing the internal volume of the reservoir 12, because the fold lines 2151 of the side panels 215 move, and because the sealing film 220 deforms. It is advantageous to choose a sealing film that is particularly flexible, i.e. almost without any shape memory, so that it can be deformed, collapsed, or creased, without generating any mechanical resistance. Naturally, as in the first embodiment, reducing the volume of the reservoir 12 causes the fluid contained in it to be put under pressure, so that it has no alternative other than to be delivered through the dispensing orifice 214, and secondarily upstream through the piece of porous material 230.

The third embodiment shown in FIGS. 9 to 12 is a variant of the preceding embodiment shown in FIGS. 5 to 8. The one-piece body 311 may be identical to the one-piece body of the second embodiment as regards the blades 311; 312, the bridges of material 3115; 3125, the side panels 315 with their fold lines 3151, and the peripheral rim 316 with its application or fixing surface 3161. The difference compared with the second embodiment lies in the head portion 313 which, in this example, forms an elongate end-piece 3134 inside which a duct 3135 extends that contains a piece of porous material 330. At the end of the end-piece 3134, a dispensing orifice 314 is formed. The dispensing end-piece 3134 makes it possible to offset the dispensing orifice 314 so that fluid can be dispensed in places to which access is difficult, such as, for example, natural orifices of the human body. Such a dispenser with an end-piece may be used for nasal sprays, for which the end-piece can be inserted into a nostril of the patient.

Reference is made below to FIGS. 13 to 16, which show a fourth embodiment of the invention. This dispenser 400 is made up of four component parts, namely a one-piece body 410, two sealing sheets 421 and 422, and optionally a piece of porous material 430.

The one-piece body 410 is made up of two blades 411 and 412 interconnected via a coupling portion 413 that forms the dispensing orifice 414. The blades 411, 412 and the coupling portion 413 with the orifice 414 may be externally identical or similar to their counterparts in the first embodiment of FIGS. 1 to 4. The blades 411 and 412 are preferably substantially plane and rigid, and the coupling portion 413 may have a rounded curved shape. The width of each of the blades is advantageously identical to the width of the coupling portion 413. However, as can be seen more clearly in FIGS. 14 and 15, the wall thickness of the blades 411 and 412 is not constant over the length of each of the blades: it can be seen that the thickness decreases going away from the coupling portion 413. In this way, the blades 411 and 412 are elastically deformable to some extent in addition to the elastic deformability of the coupling portion 413. Thus, by pressing on the blades 411 and 412 so as to bring them closer together, not only is the head portion 413 naturally deformed, thereby tending to accentuate its rounded shape, but also the ends of the blades that are remote from the head portion 413 are also deformed.

In the invention, the blades are provided with projecting tabs 4133 that co-operate to define a recess inside which a piece of porous material 430 is received, which, in this example, is in the form of a segment of a cylinder. Thus, the tabs 4133 act as retaining means making it possible to hold the piece of porous material 430 adjacent to the dispensing orifice 414. As in the preceding embodiments, the piece of porous material 430 is suitable for being impregnated with fluid in liquid or powder form before said fluid is delivered through the dispensing orifice 14 when the blade 411 is brought towards the blade 412. It may sometimes be omitted.

In this embodiment, the ends of the blades that are remote from the head or coupling portion 413 are connected together via an elastically deformable coupling web 416 which, in this example, extends over a circular arc. The elastic coupling web 416 participates in the elastic deformation or return characteristic of the one-piece body 410: provision may even be made for the coupling web 416 to perform the elastic return function on its own. With the coupling web 416, the one-piece body 410 forms a closed cylindrical loop. Thus, the one-piece body 410 can be made from an extruded shaped-section member cut up into slices or segments to the desired width. It is also possible to imagine forming the one-piece body 410 by injection molding.

Because of its closed cylindrical shape, the one-piece body 410 forms two end edges 4161 and 4162, each or which extends in a respective plane. Preferably, the two planes formed in this way are parallel to each other. This can be seen very clearly in FIG. 16.

In the invention, each end edge is provided with a sealing film 421, 422 which is fixed in leaktight manner so as to define an internal volume that serves as a fluid reservoir 12. The fluid may fill almost all of the reservoir 12, or, in a variant, the fluid may share the reservoir 12 with a gas (advantageously air) so as to generate a two-phase spray at the outlet of the dispensing orifice 414.

Figure 16:
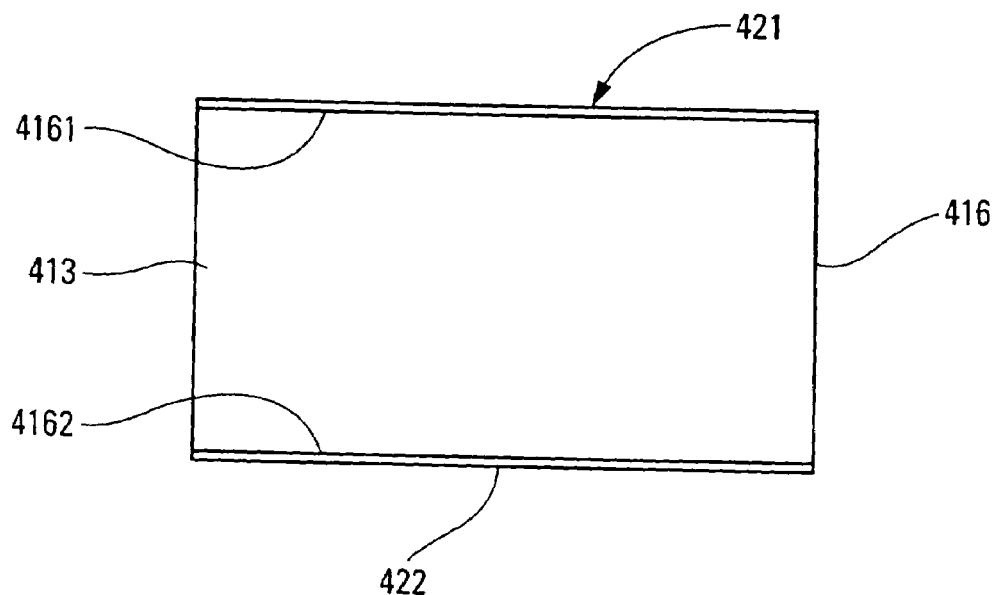
FIG. 16 is a plan view of the dispenser of FIG. 13.

It should be noted that it is particularly advantageous for the end edges 4161 and 4162 to extend in planes because they serve as application or fixing surfaces or zones for the two sealing films 421 and 422. It is much easier to fix a film on a plane surface than on a shaped or undulating surface. The dispenser in this embodiment is then, as shown in FIG. 16, in the form of a thick slice constituted by the one-piece body 410 flanked on its top and its bottom sides by respective sealing films 421 and 422 fixed in leaktight manner.

In this embodiment, the elastic deformation or return characteristic may be imparted individually or cumulatively by the head or coupling portion 413, the blades 411, 412, the coupling web 416, or indeed the retaining tabs 4133 which may deform or come into elastic abutment against the piece of porous material 430 which may also be elastically deformed by the ends of the retaining tabs.

As in the preceding embodiments, the blade 411 defines an actuating wall while the blade 412 defines a backing wall, or vice versa. It can also be said that the dispenser defines two actuating walls defined by the blades 411 and 412. This also applies to the three preceding embodiments.

In this fourth embodiment, as in the preceding embodiments, the two blades 411 and 412 are symmetrically identical. It is however possible to imagine an embodiment in which the blades have shapes that are different from each other. It is also possible to imagine the blades having different functions: e.g. the blade 411 or the blade 412 may be the sole actuating wall, while the other blade constitutes a genuine backing wall whose dynamic behavior relative to the head is different from the other blade.

By means of the invention, a dispenser may be made using techniques that are very simple (injection molding, cutting and folding, slicing, adhesive bonding, and flat sealing) and with a very small number of parts (a maximum of four and a minimum of two).

The invention claimed is:

1. A fluid dispenser (100; 200; 300; 400) for dispensing a fluid in liquid or in powder form, said dispenser including a reservoir (12) serving to contain fluid, and a dispensing orifice (114; 214; 314; 414) via which the fluid is dispensed, said reservoir (12) having an actuating wall (111; 211; 311; 411) and a backing wall (112; 212; 312; 412), said walls be adapted to be brought towards each other by elastic deformation to reduce the volume of the reservoir, and thus to deliver fluid through the dispensing orifice, said dispenser further comprising a one-piece body (110; 210; 310; 410) and at least one flexible sealing film (120; 220; 320; 421; 422), the actuating wall and the backing wall being formed by the one-piece body, characterized in that the actuating wall and the backing wall are angularly positioned relative to each by forming an angle that decreases when they are brought towards each other; and wherein the body and the at least one film together form the reservoir.

2. A dispenser according to claim 1, in which the dispensing orifice is formed by the one-piece body.

3. A dispenser according to claim 1, in which the body defines a head portion (113; 213; 313; 413) which connects the actuating wall to the backing wall, said head portion remaining substantially static while the actuating wall and the backing wall are being brought elastically towards each other, the dispensing orifice being formed by the head portion.

4. A dispenser according to claim 3, in which the actuating wall (111; 211; 311; 411) is hinged elastically to the head portion.

5. A dispenser according to claim 3, in which the actuating wall (111; 211; 311; 411) is elastically deformable.

6. A dispenser according to claim 4, in which the backing wall (112; 212; 312; 412) is symmetrically identical to the actuating wall about the head portion.

7. A dispenser according to claim 3, in which the actuating wall and the backing wall converge mutually at the head portion.

8. A dispenser according to claim 1, in which the actuating wall and the backing wall are substantially plane and rigid.

9. A dispenser according to claim 1, including a piece of porous material (130; 230; 330; 430) suitable for being impregnated with fluid, said piece being disposed adjacent to the dispensing orifice (114; 214; 314; 414).

10. A dispenser according to claim 9, in which the body defines a head portion (113; 213; 313; 413) forming the dispensing orifice (114; 214; 314; 414), said portion forming retaining means (2133; 3134; 4133) for holding the piece of porous material (130; 230; 330; 430) adjacent to the dispensing orifice.

11. A dispenser according to claim 3, in which the head portion forms an elongated end-piece (3134) at the free end of which the dispensing orifice is formed (314).

12. A dispenser according to claim 1, in which the actuating wall and the backing wall are interconnected by deformable side panels (215; 315).

13. A dispenser according to claim 1, in which the body (210; 310; 410) is provided with at least one plane peripheral fixing zone (2161; 3161; 4161, 4162) to which a plane sealing film (220; 320; 421, 422) is fixed.

14. A dispenser according to claim 1, in which the body (210; 310) is made by injection molding.

15. A dispenser according to claim 1, in which the body (110) is made from a plane sheet that is cut and then folded, the dispensing orifice (114) being situated at the fold.

16. A dispenser according to claim 1, in which the body (110; 410) is made from an extruded shaped-section member.

17. A dispenser according to claim 1, in which the actuating wall (411) and the backing wall (412) are connected together via an elastically deformable coupling web (416) formed by the one-piece body (410).

18. A dispenser according to claim 1, made up only of the one-piece body, of one or more sealing films, and optionally of a piece of porous material suitable for being impregnated with fluid and disposed in the immediate vicinity of the dispensing orifice.

19. A dispenser according to claim 1, in which the elastic deformation is provided by the one-piece body which has elastic resilience suitable for returning it to a rest position, in which the actuating wall is as far away as it can be from the backing wall.

20. A dispenser according to claim 1, in which the actuating wall is mounted to pivot relative to the backing wall.

21. A dispenser according to claim 3, in which the head portion is elastically deformable.

22. A fluid dispenser having a one-piece body comprising two blades respectively defining actuating and backing walls, said two blades being connected together at a coupling portion so that the blades pivot relative to each other by elastic deformation of the coupling portion, said two blades being connected together by a sealing film, the body and the film forming together a fluid reservoir.

23. A fluid dispenser comprising a body constituted by a slice of deformable loop cylinder having two opposite loop edges (4161, 4162) on which two sealing films (421, 422) are respectively secured to close the cylinder and form a fluid reservoir, the cylinder having a dispensing orifice between the two edges.

24. The dispenser according to claim 1, wherein the at least one film is fixed to the body and forms a wall of the reservoir.

25. The dispenser according to claim 22, wherein the film forms a wall of the reservoir.

26. The dispenser according to claim 22, wherein the two blades are connected together by two sealing films.

* * * * *